(12) United States Patent
Olive

(10) Patent No.: US 6,360,688 B1
(45) Date of Patent: Mar. 26, 2002

(54) PHOTOPERIODIC CONTROL OF GROWTH

(75) Inventor: Peter James William Olive, Tyne and Wear (GB)

(73) Assignee: Seabait Limited, Ashington (GB)

( * ) Notice: Subject to any disclaimer, the term of this patent is extended or adjusted under 35 U.S.C. 154(b) by 0 days.

(21) Appl. No.: 09/402,595

(22) PCT Filed: Apr. 3, 1998

(86) PCT No.: PCT/GB98/00984

§ 371 Date: Dec. 20, 1999

§ 102(e) Date: Dec. 20, 1999

(87) PCT Pub. No.: WO98/44789

PCT Pub. Date: Oct. 15, 1998

(30) Foreign Application Priority Data

Apr. 4, 1997 (GB) .............................................. 9706848

(51) Int. Cl.⁷ ............................ C12N 5/00; A01K 29/00
(52) U.S. Cl. ..................... 119/6.7; 435/375; 435/395
(58) Field of Search ................................ 435/375, 395; 119/6.7

(56) References Cited

U.S. PATENT DOCUMENTS 3,765,372 A    10/1973   Moe, Jr. et al. ................. 119/3

FOREIGN PATENT DOCUMENTS

WO          98/06255        2/1998

OTHER PUBLICATIONS

Chu et al., Photoperiod and temperature regulation of growth and reproduction in Streblospio benedicti (Polychaeta: Spionidae) May 1989, Invertebrate Reproduction and Development, vol. 15, No. 2, p. 131–142.*

* cited by examiner

*Primary Examiner*—Deborah J. R. Clark
*Assistant Examiner*—Shin-Lin Chen
(74) *Attorney, Agent, or Firm*—Ratner & Prestia

(57) ABSTRACT

A method of controlling a growth rate and other characteristics of marine worms is disclosed. The method concerns the control of light to which the worms are subjected, and allows the rate growth to be manipulated (i.e. increased) outwith the normal growing season.

23 Claims, 12 Drawing Sheets

PHOTOPERIODIC CONTROL OF GROWTH

This invention relates to aquaculture of marine worms and particularly although not exclusively methods for controlling growth of marine worms.

Marine bait worms are animals in the Class Polychaeta of the Phylum Annelida or in the Phylum Sipunculida or are such other animals as may be generally referred to as worms which may be used as bait by anglers. Such worms are also used as feedstuffs for fish, crustaceans and other organisms, for toxicity testing and for other scientific purposes.

Naturally occurring supplies of marine worms are not inexhaustible and collection of marine worms has been recognised as a cause of serious environmental concern.

Aquaculture of marine worms provides a sustainable source. However, the seasonal breeding cycle of marine worms hinders provision of a constant supply of worms throughout the year. Since the natural fecundity of female marine worms is very high, large numbers of fertilised eggs are available from time to time that are surplus to requirements and are usually wasted. The use of cryopreservation techniques and other methods for the preservation of larvae may provide effective supplies of juveniles throughout the year.

A further constraint and hindrance to the maximum production of worms throughout the year is the seasonal variation of growth rate that may occur in cultured marine worms and which may be related to the onset of sexual development or may be observed to occur even in the absence of signs of sexual maturation.

According to a first aspect, the present invention provides a method of controlling the growth of polychaete worms as recited in claim 1.

The quality, quantity and/or duration of the light may be controlled in the method.

Preferred features which may be used with aspects of the invention are set out in the dependent Claims.

The worms are preferably maintained in a controlled temperature regime, and may have an effective date of birth other than during the natural breeding season. The worms can be recovered from a preservation system, such as a cryopreservation system.

The worms are preferably induced to breed outside the normal breeding season as well as within the normal breeding season.

Preferably, the photoperiodic regime to which the worms are subjected is substantially equivalent to the natural photoperiodic regime and optionally comprises one or more periods of light and one or more periods of dark within a 24 hour or near to 24 hour day. The duration of the periods of light and the periods of dark may be controlled and changed from day to day as required.

The photoperiodic regime may be one that is substantially equivalent to the natural photoperiodic regime but is displaced in time (eg by three to six months) relative to the natural photoperiodic regime.

The photoperiodic regime may comprise periods of time when the duration of light in the 24 hour or near to 24 hour photoperiodic day is held constant and in which the duration of light is greater than 12 hours.

The period of natural daylight may be supplemented by artificial lights during a period prior to dawn and or after dark.

The photoperiodic regime may be one in which natural daylight is excluded and light is provided entirely by artificial lights, the duration of lighting being adjusted such that the total duration of light is greater than 12 hours in any one 24 hour or near to 24 hour period.

The photoperiodic regime may be one in which short periods of light are given at regular intervals to simulate a fixed pattern of light and dark by means of a skeleton photoperiod.

The photoperiodic regime may be one in which a short exposure to light occurs shortly or some hours after the transition to dark having the effect of resetting the time at which the dusk light dark transition is effective.

The photoperiodic regime may be one in which a short exposure to light occurs shortly before, or some hours before, the transition to light having the effect of resetting the time at which the dawn dark light transition is effective.

The duration of the period of short days or the duration of the period of long days can be varied. The photophase may be kept substantially constant during a period of short days, or a period of long days.

The worms can be members of the order Phyllodocida e.g. the Nereidae family, and especially the species *Nereis (Neanthes) virens*.

Alternatively the worms are members of the order of Eunicide, e.g. family Eunicidae genus Marphysa and/or the family Onuphidae genus Diapatra.

The invention advantageously results in increased rate of weight gain and/or increased segment proliferation/regeneration rate and/or increased rate of feeding and/or activity during periods when the naturally occurring duration of light is such that the rate of weight gain and/or increased segment proliferation/regeneration rate and/or increased rate of feeding and activity is lower than the optimum rate that can be achieved.

Exposure of the worms to light regimes in which the duration of continuous light or the interval between the period of light interpreted as dawn and the period of light interpreted as dusk is greater than the critical value below which the growth rate and/or regeneration rate and/or feeding rate and/or activity rate is reduced can result in an increased growth rate and/or regeneration rate and/or feeding rate and/or activity rate.

In the example of the ragworm *Nereis virens* the advantageous results that can be achieved by the application to the invention will normally be maximally achieved during periods when the duration of light in the photoperiodic day is 12 hours of light or less.

In the example of the ragworm *Nereis virens* the advantageous results that can be achieved by the application of the invention will be achieved to a lesser though commercially significant degree during periods when the duration of light in the photoperiodic day is between 12 hours and 16 hours of light.

In the example of the ragworm *Nereis virens* the advantageous results that can be achieved by the application of the invention may be achieved at any time be exposure of animals to photoperiodic conditions in which the duration of the light is greater than 16 hours of light in a 24 hour period.

In the example of the ragworm *Nereis virens* exposure of the worms to any light regime in which the duration of continuous light, or the interval between the period of light interpreted as dawn and the period of light interpreted as dusk, is greater than the critical value of 12 hours of light per 24 hour day during periods when the photoperiod is naturally less than 12 hours per day can result in an increased growth rate and/or regeneration rate and/or feeding rate and/or activity rate to the advantage of the producer. The degree of advantage can be dependent on the natural duration of the period of light at the time of application of the invention and on the duration of the artificial exposure to light or the duration of the effective duration of the light as achieved by the application of a skeleton photoperiod or the extension of the effective duration of the period of light by the exposure of the animals to short periods of light before dawn or after dusk.

Certain embodiments of the invention permit the producer of worms to maintain the rates of growth and/or regeneration and/or segment proliferation and/or feeding and/or activity of the worms to be maintained at a high level at all seasons of the year and in all stocks whatever the actual date of birth and/or recovery from a preservation system subject only to the normal constraints of the temperature regime and/or feeding regime to which the animals are subjected.

Long day treatments can induce greater growth in terms of weight gain, segment proliferation and/or regeneration of truncated worms.

In order to facilitate description the following terms are defined:

Photoperiodic Day
- the duration of a single sequence of light and dark usually with a total duration close to 24 hours. The relative duration of the periods of light and dark in the 24 hour photoperiodic day may be described as LD x:y where x is the duration of light and y is the duration of dark. Thus a 24 hour photoperiodic day LD 8:16 is a sequence of 8 hours of light and 16 hours of dark and a 24 hour photoperiodic day LD 16:8 is a sequence of 16 hours light and 8 hours dark, each repeated every 24 hours.

The period of light in the LD cycle may be referred to as the Photophase.

The period of dark in the LD cycle may be referred to as the scotophase.

Natural Photoperiodic Regime
- the annual sequence of photoperiodic days that occurs naturally at the location at which the animals are kept or the work is being carried out;

Effective Date of Birth
- the actual date of fertilisation of an animal or the date of recovery of the animal from a preservation system;

Photophase
- the duration of a period of light in the photoperiodic day;

Scotophase
- the duration of dark in the photoperiadic day;

Critical Photophase
- the duration of a photophase which is such that any greater photophase will be interpreted as being a long day and which is such that any shorter photophase is interpreted as a short day and which, in the specific case of the reaction of *Nereis* (*Neanthes*) *virens* described herein is a photophase of between 12–13 hours in a 24 hour day;

Short Day
- a 24 hour photoperiodic day in which the photophase is substantially less than the critical photophase length ie 12 hours or less for *Nereis* (*Neanthes*) *virens* for growth of eggs;

Long Day
- a 24 hour photoperiodic day in which the photophase is substantially greater than the critical photophase ie 13 or more hours for *Nereis* (*Neanthes*) *virens* for growth of eggs;

Optionally, the photophase is controlled. In an embodiment of the invention the photophase can be varied (ie increased) to control the growth while the scotophase can be maintained constant. Alternatively, the scotophase can be varied (ie deceased) while the photophase remains constant. Alternatively, the photophase and scotophase can both be varied. The photoperiod can be 24 h or some other advantageous period.

In an embodiment of the invention the duration of the photophase in a 24 hour LD cycle is maintained above 12 hours light and the duration of the scotophase is correspondingly less than 12 hours darkness. The duration of the photophase is preferably 13 hours of light or substantially greater than 13 hours of light. The total duration of the photophase and of the scotophase may be constant each day or alternatively may be allowed to vary progressively as occurs naturally between the spring and autumn equinox in the Northern hemisphere.

The photoperiodic day may be 24 hours or some other period close to 24 hours or my be a period that is a multiple of 24 hours such as 48 hours or 72 hours.

An embodiment of the invention will now be described by way of example and without limitation.

EXAMPLE 1

Figure 1:
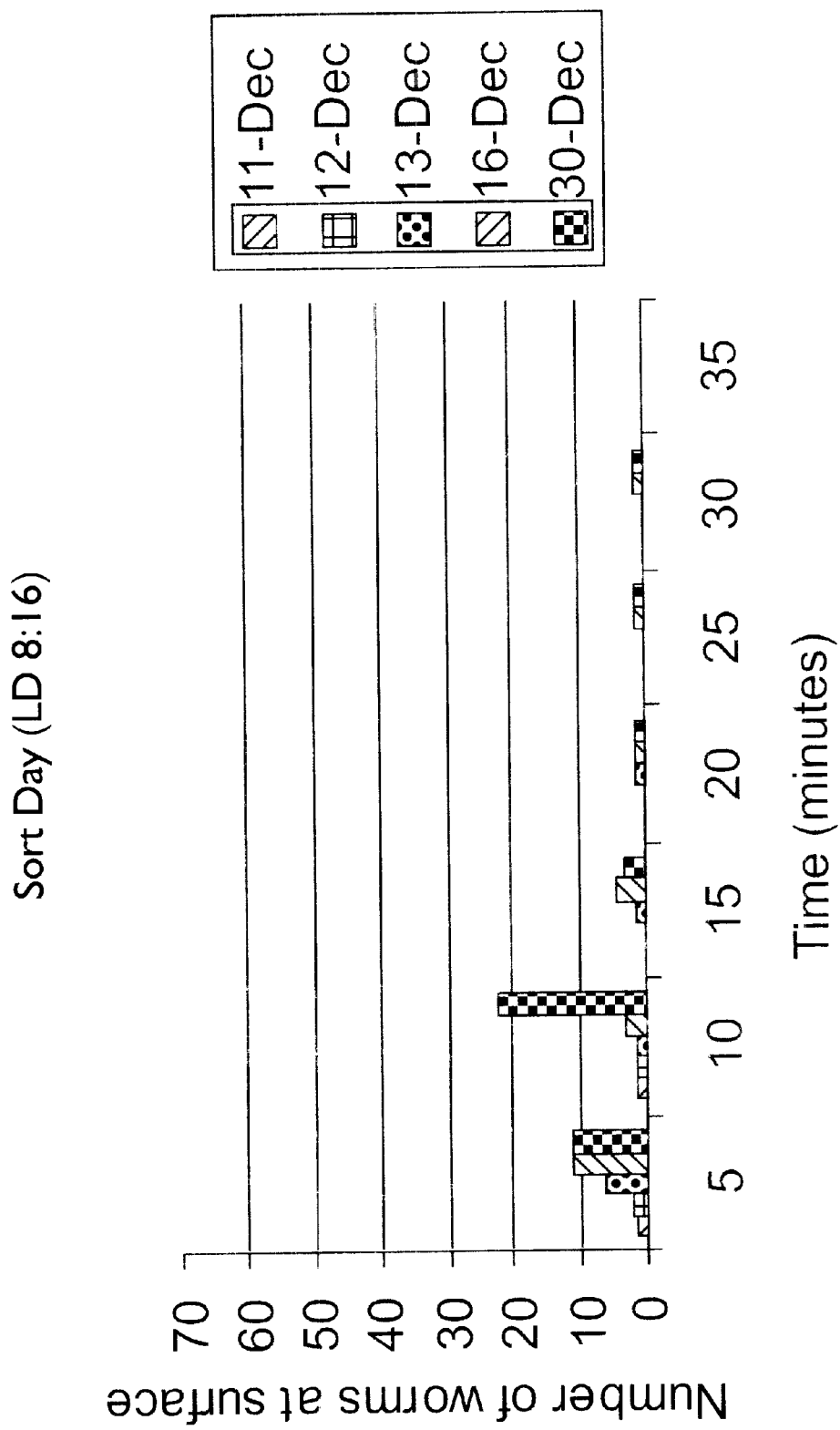
FIG. 1 shows the time worms spent feeding at the surface in a short day (LD 8:16).

Between Apr. 11, 1996 and Nov. 11, 1996, one hundred polychaetes, species *Nereis virens* transferred from a commercial farm to a marine laboratory. All worms were anaesthetised in 5% seawater/alcohol, their segments individually counted and parapodia (paddle like appendages, one pair per segment) marked by clipping for easy identification of individual animals. The worms were then weighed and damp dried values used for all further data analysis. The animals were maintained throughout the experiments in sieved washed sand in shallow containers ⅓ meter squared. Filtered sea water was used in all aquaria. Each aquarium contained fifty worms.

Worms were subjected to a different light regime in photo and temperature controlled environmental cabinets. One cabinet constituted long days, the other, short. Long days were represented by 16 hours of light and 8 hours of darkness whilst short days, 8 hours light, 16 hours darkness. Long days mimic summer conditions, short days, winter. For both regimes two fluorescent 100 watt light sources were used at an approximate distance of one meter from the aquaria. The temperature was maintained at 14–15 degrees centigrade.

Both assays were fed the same rations (pelleted trout feed) throughout the experimental procedure at between 2–8% body weight per day. The rations were increased as the worms grew in weight. Uneaten food was siphoned off the following day and a partial water change was made daily. Further to maintaining water quality, two biological gravel filters were incorporated into each aquaria.

At the same time newly developing juvenile nectochaete larvae were taken from the farm. These had been reared through the trochophore stage (two weeks) and are essentially 6–7 months out of phase with their natural populations usually developing in the spring. The nectochaetes were maintained in long and short days (in the same environmental cabinets as the juveniles) with a density of approximately 1100 individuals per aquaria. Crushed pelleted trout food was fed every week and as the worms grew, food was administered more frequently. After 4 months the developing juveniles were "thinned out" into larger boxes. Again, temperature was maintained between 14–15 degrees centigrade.

Finally, 36 juveniles were taken from the farm on Nov. 22, 1996 and irrespective of their original segment number all truncated to 50 segments from the head region. These truncated worms, of approximately equal weight, were maintained in glass tubes (acting as artificial burrows) in sea water filled aquaria. Their rations, as for the juveniles and nectochaetes, were increased as the worms regenerated segments and grew in weight. 18 worms were maintained in long days and 18 in short, with a constant temperature of between 14–15 degrees centigrade.

Regular behavioural assays were carried out in the juveniles and used to determine a shift in feeding behaviour between long and short days. Immediately after the worms had been fed, a quantitative visual count was made of the number of animals that came out of their burrows to feed, each assay lasting for a total of 35 minutes. Weighing and counting for both naturally accrued and regenerated segments was carried out monthly with all results represented graphically.

A behavioural assay was used to show the sudden shift in feeding rate as the worms were brought from the farm (effective short day conditions) into long day regime. The number of animals that came out of their burrow to feed over the first 35 mins after feeding (peak of feeding activity) was measured in both circumstances and the results showed that the photoperiodic treatment long days significantly increases the number of animals feeding.

Figure 2:
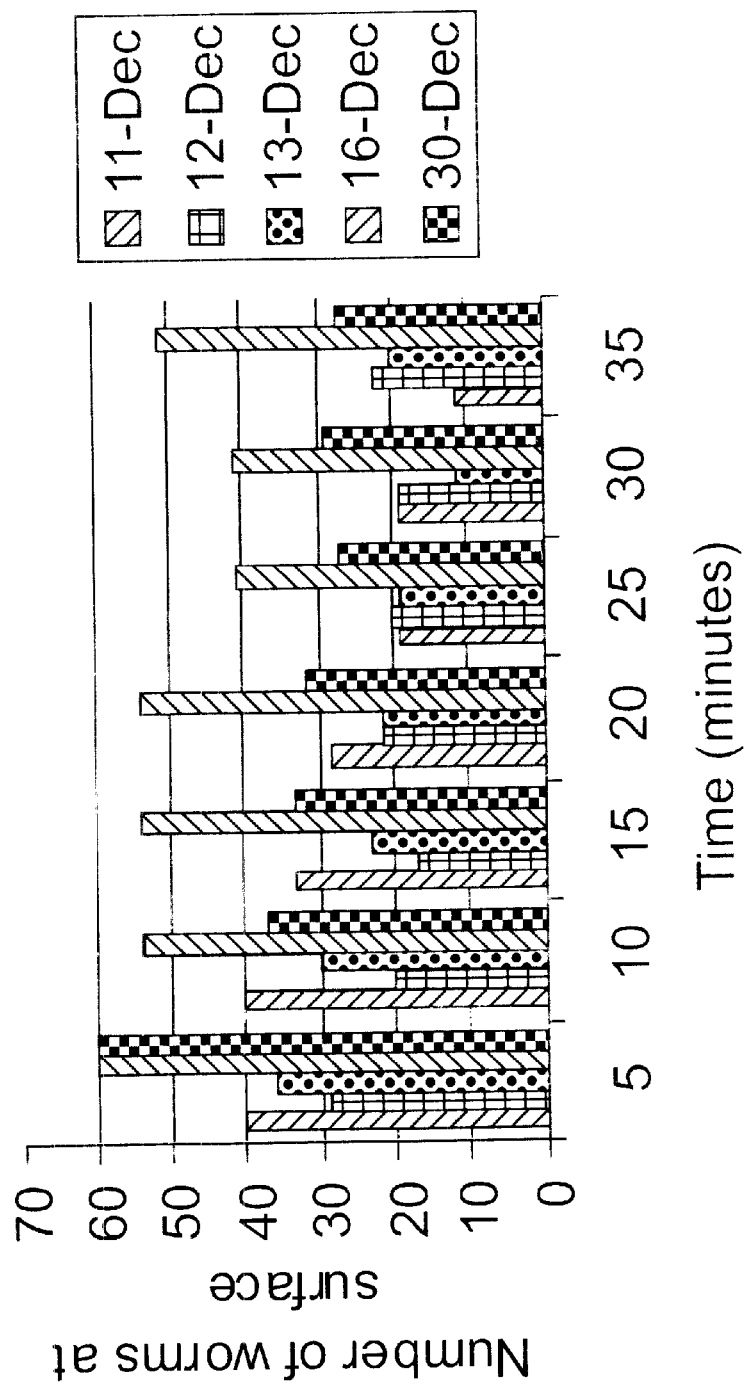
FIG. 2 shows the time spent by worms feeding at the surface in a long day (LD 16:8).

FIG. 1 and FIG. 2 show results for December.

Figure 3A:
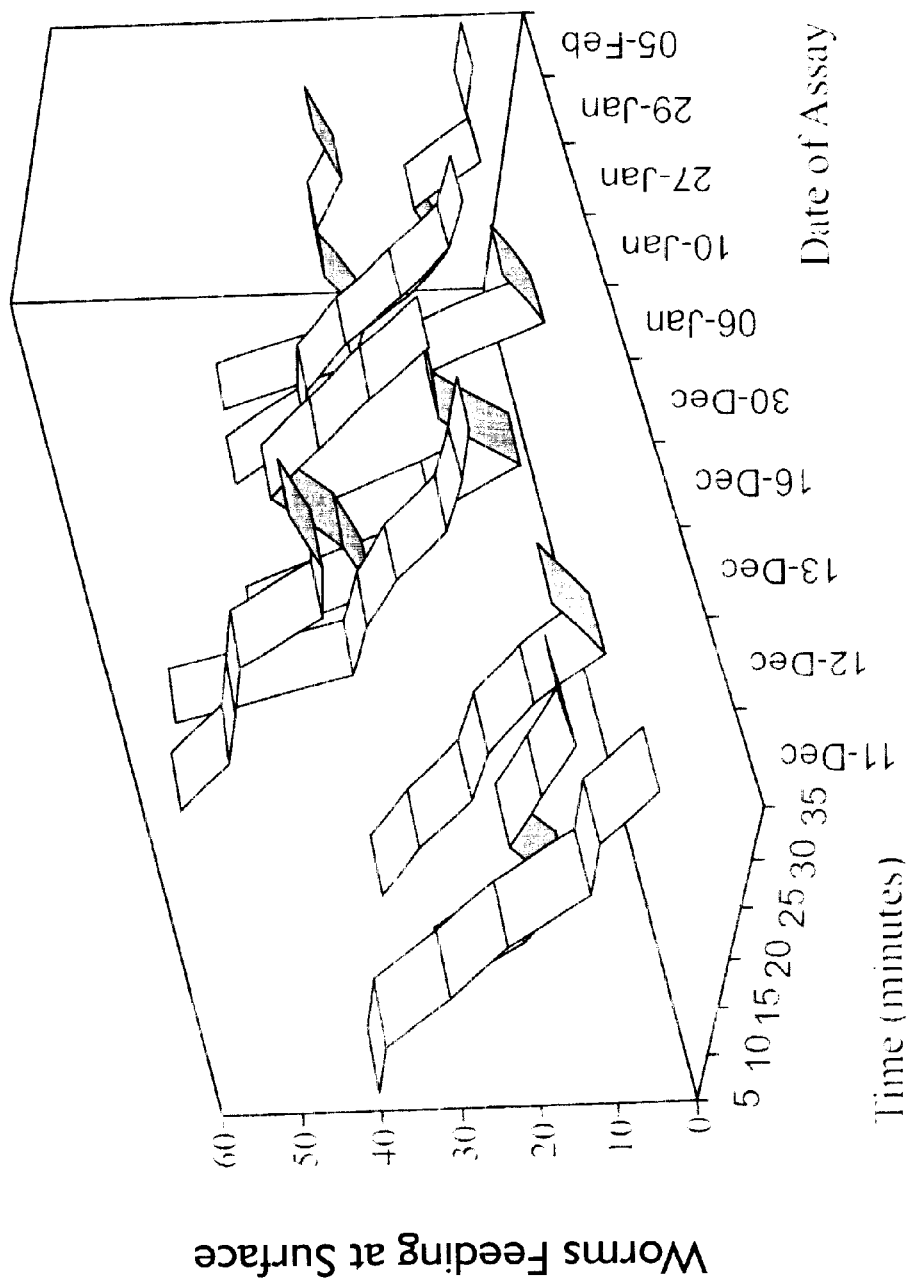
FIG. 3 shows a composite of worms' feeding behaviour for (a) long day and (b) short day.
Figure 3B:
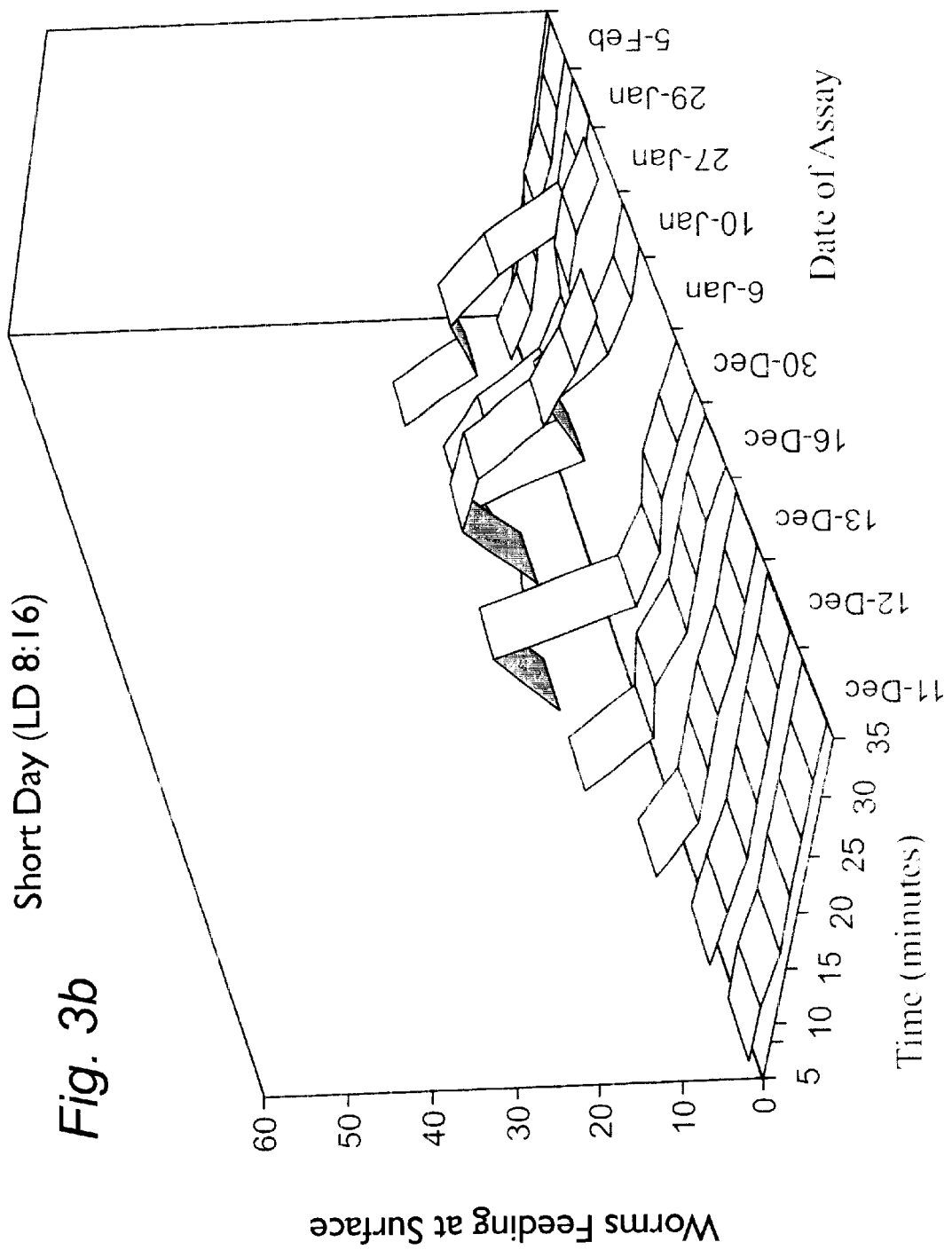

FIGS. 3a and 3b shows a composite of the several months' behavioural assays. The feeding behaviour of the short day (S/D) warms is far lower than that of the long day (L/D).

The rise in activity through January and into February in FIG. 3b may suggest that the worms are responding to an interval timer or perhaps a circa-annual rhythm that is preparing them for the onset of summer.

Figure 4:
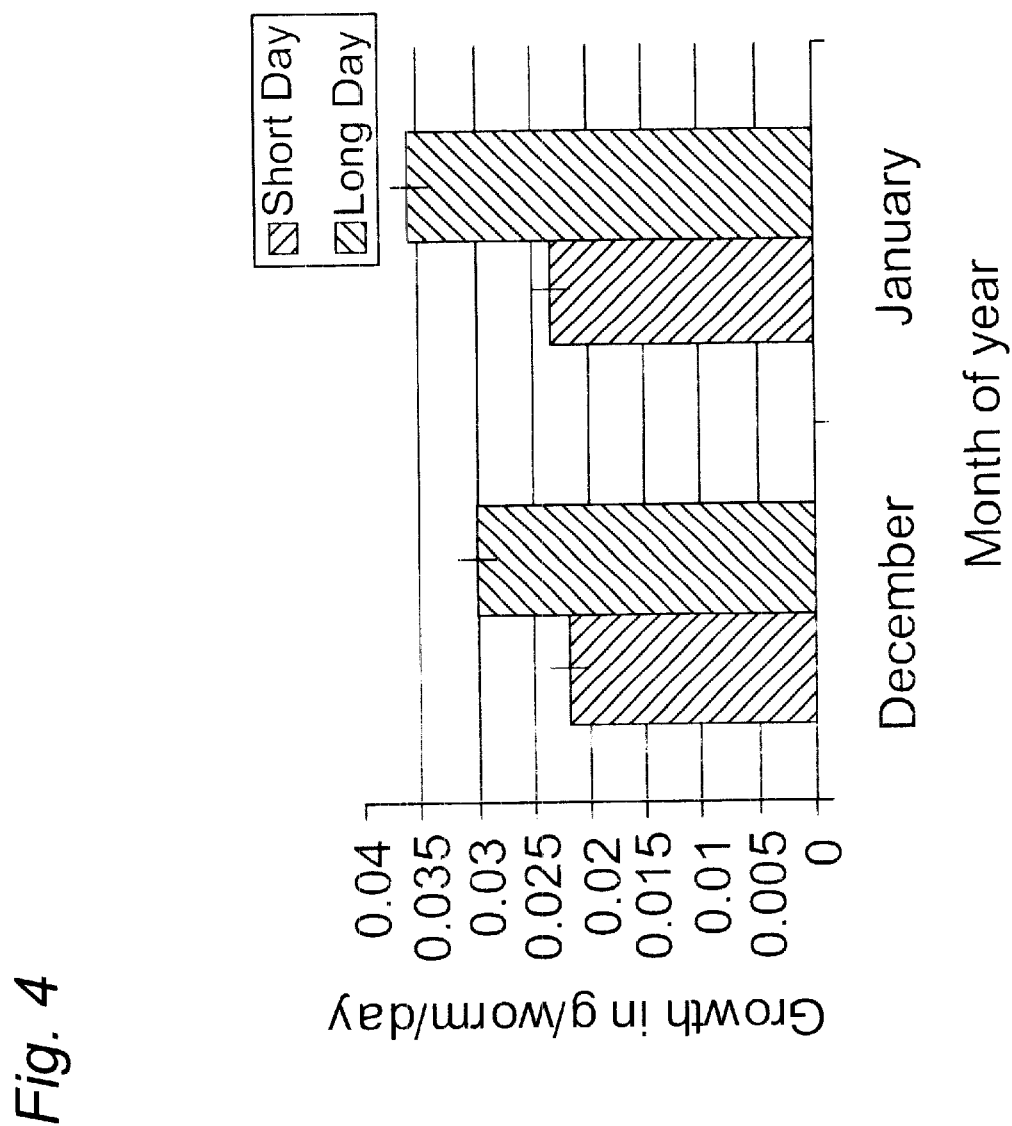
FIG. 4 compares the growth rate of juvenile *Nereis virens* for short and long days.
Figure 5:
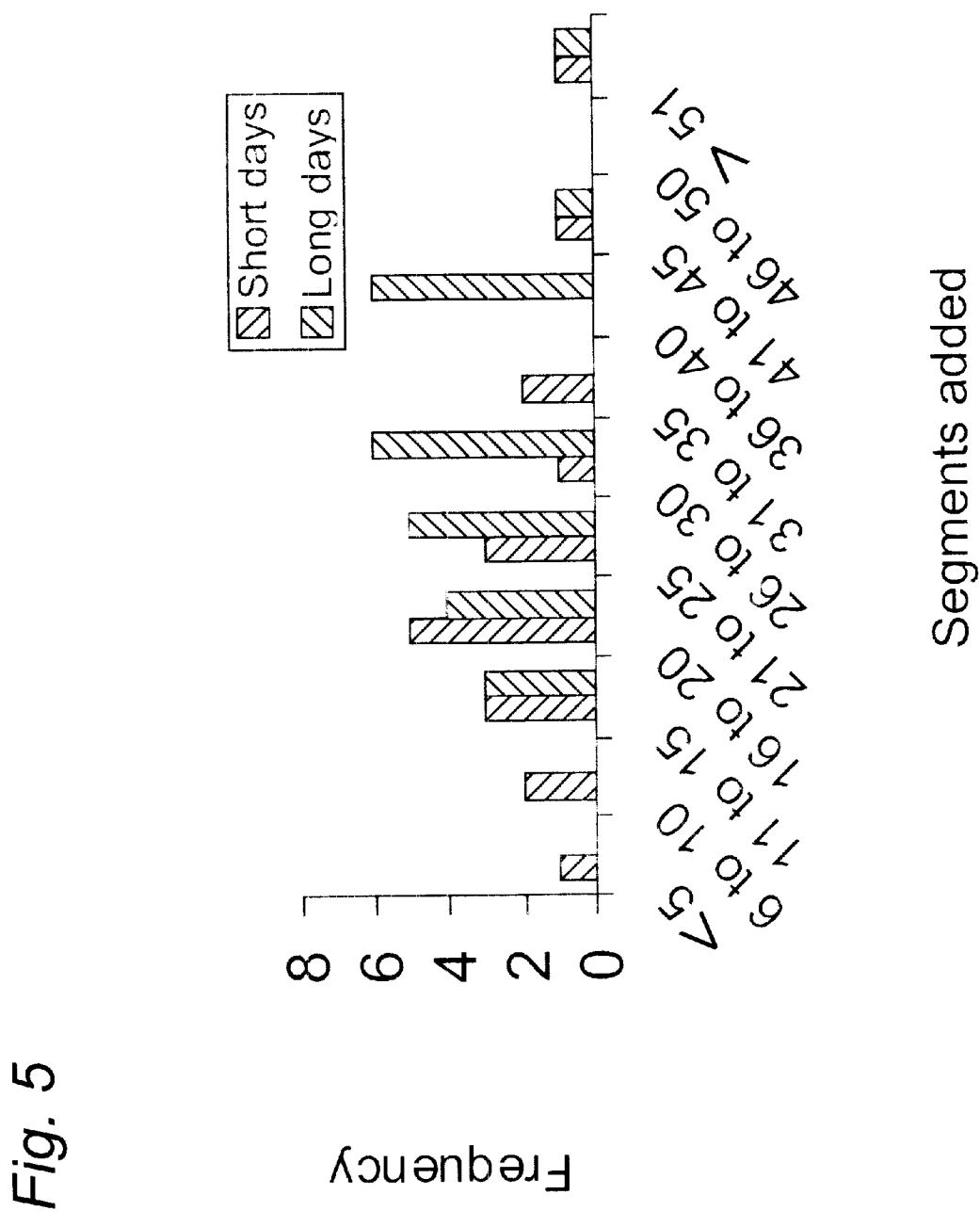
FIG. 5 shows the rate of segment addition by juvenile worms in short and long days.

FIG. 4 shows the growth rate of juvenile *Nereis virens* in short and long days. FIG. 5 shows the rate of segment addition by juvenile worms in short and long days.

Figure 6:
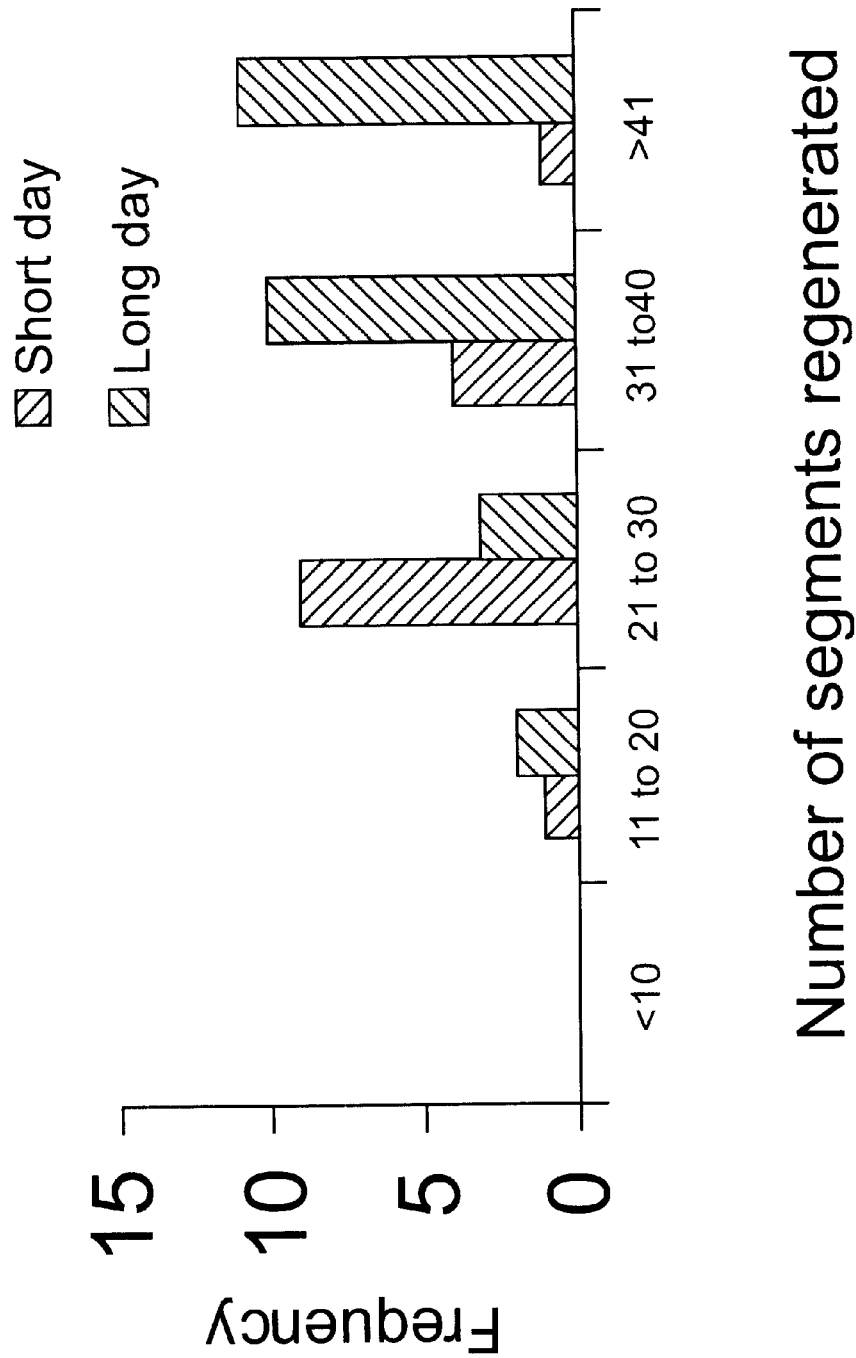
FIG. 6 compares the number of segments regenerated for worms exposed to a short day or long day regime.

FIG. 6 shows that regenerated worms show an even greater response to the different photo-regimes. The majority of worms for the L/D had regenerated more than 40 segments whilst for the SID the majority had between 21–30 segment additions.

Figure 7:
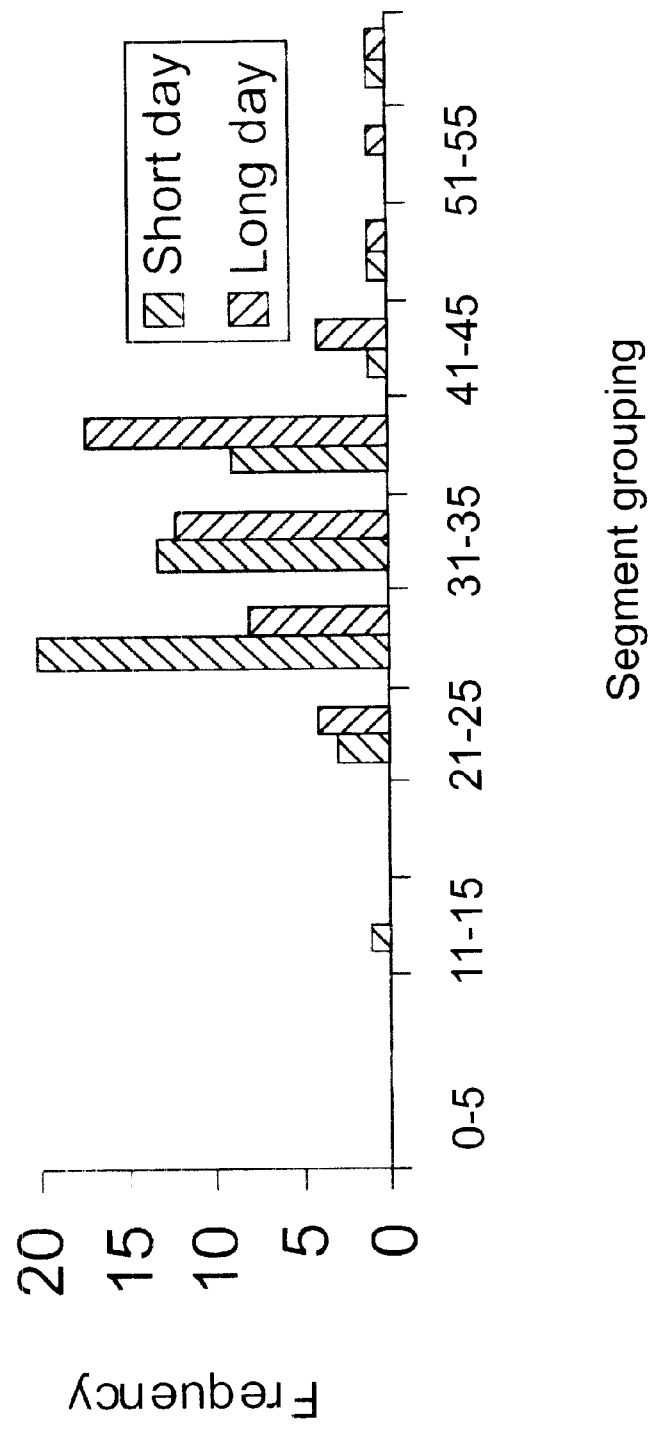
FIG. 7 compares the segment grouping for a nectocheto lava reared in short day or long day photoregimes.

FIG. 7 shows results from nectochaete larvae which were reared from the late trochophore stage and after 14 weeks L/D and S/D segment number compared. Once again, the L/D juveniles were significantly larger.

EXAMPLE 2

A second embodiment of the invention will now be described by way of example and without limitation.

The activity of individual animals was measured automatically by means of an actograph. The actograph consisted of an arrangement of infra-red light sensors arranged around the openings of U-shaped glass burrows inserted into the base of an aquarium tank. The signals generated by the infra-red light sensors were recorded in a data logger and subsequently downloaded to a computer for analysis. Marine worms of the species *Nereis virens* were introduced to U-shaped glass burrows in equipment as described above and the whole apparatus introduced to controlled temperature chambers supplied with sea water at 18° C. and in which the light was provided by fluorescent tubes controlled by time switches.

Four animals were introduced into each of two controlled temperature chambers and their activity was recorded.

The duration of the light and dark periods was changed from time to time by means of the light controls and the groups of animals were exposed to a variety of photoperiodic regimes in which the duration of the photophase and consequently the duration of the scotophase was varied within a fixed 24 hour photoperiodic day in the absence of natural daylight. The activity of the animals was recorded constantly and separately for the animals in the two different light regimes for periods of several days by means of the apparatus.

The apparatus recorded an event each time a worm passed through the infra red light detector and recorded the duration of time between events by recording whether each channel was open or closed each second for periods up to several days. The accumulated data was used to construct a graph of the activity of the animals during time.

Figure 8A:
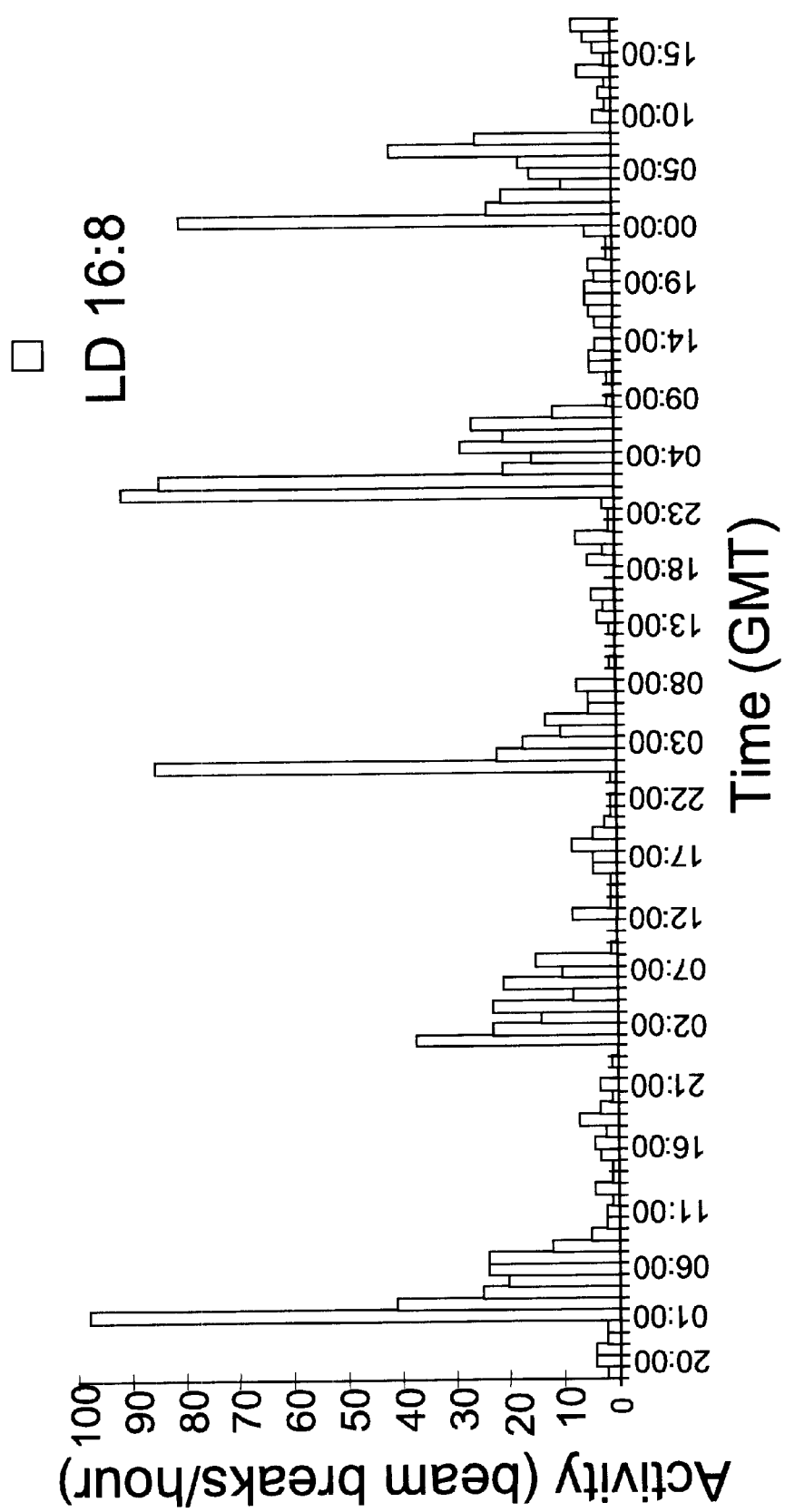
FIG. 8a shows the activity of worms measured by infrared light detector when exposed to a long day cycle (LD 16:8).
Figure 8B:
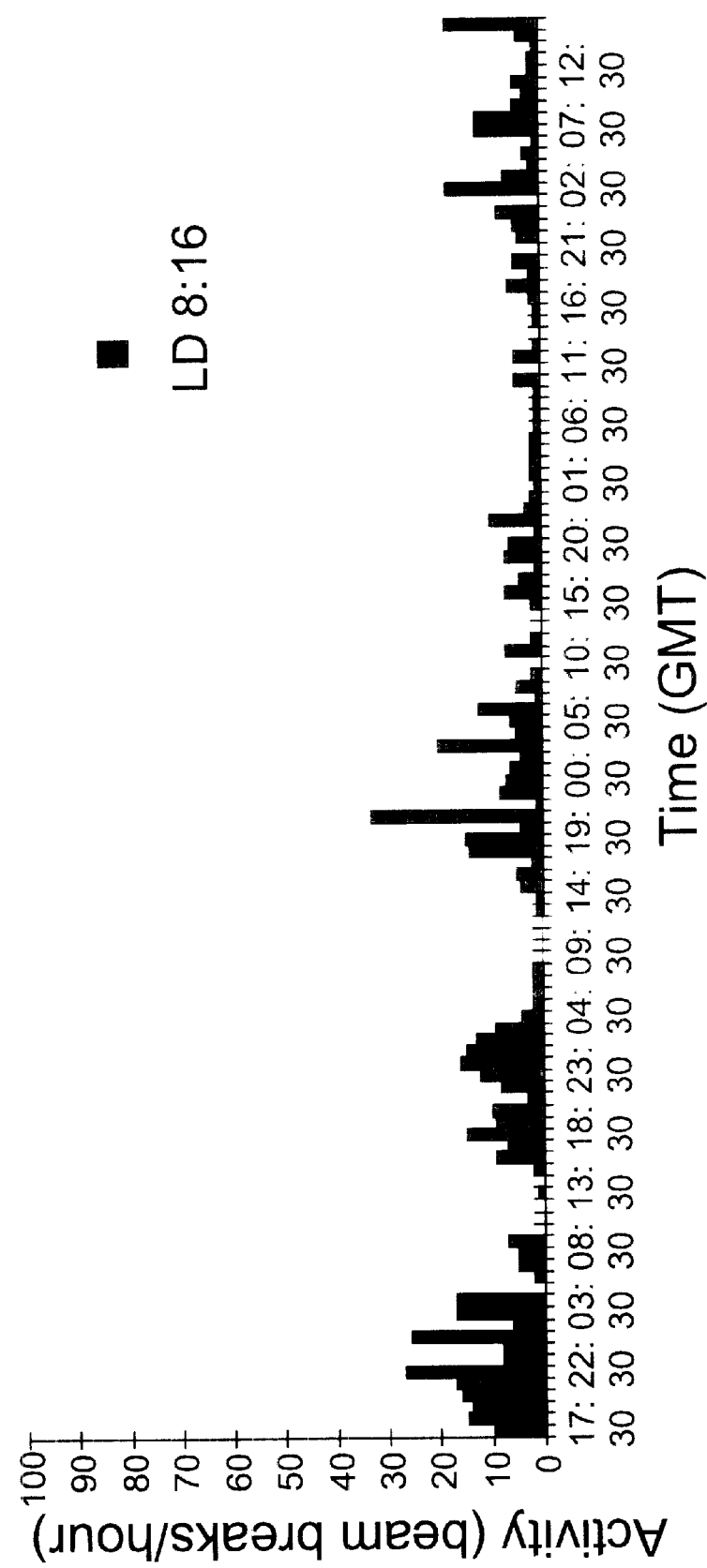
FIG. 8b shows the activity of worms as measured by an infrared light detector for a short day cycle (LD 8:16).

FIG. 8a is an example of a set of data recorded for animals exposed to an LD cycle 16:8 and FIG. 8b is an example of a set of data recorded for animals exposed to an LD cycle of 8:16. The figure and data provide convincing evidence that the animals exhibit a nocturnal pattern of diurnal behaviour and provide further evidence that the total level of activity is substantially greater during the relatively short scotophase of the LD cycle 16.8 and that the total level of activity is lower during the relatively long scotophase of the LD cycle 8:16.

EXAMPLE 3

In a further series of observations the activity patterns were recorded for animals exposed to LD cycles comprising LD 8:16, LD 12:12, LD 13:11, LD 14:10, LD 15:9 and LD 16:8.

Figure 9:
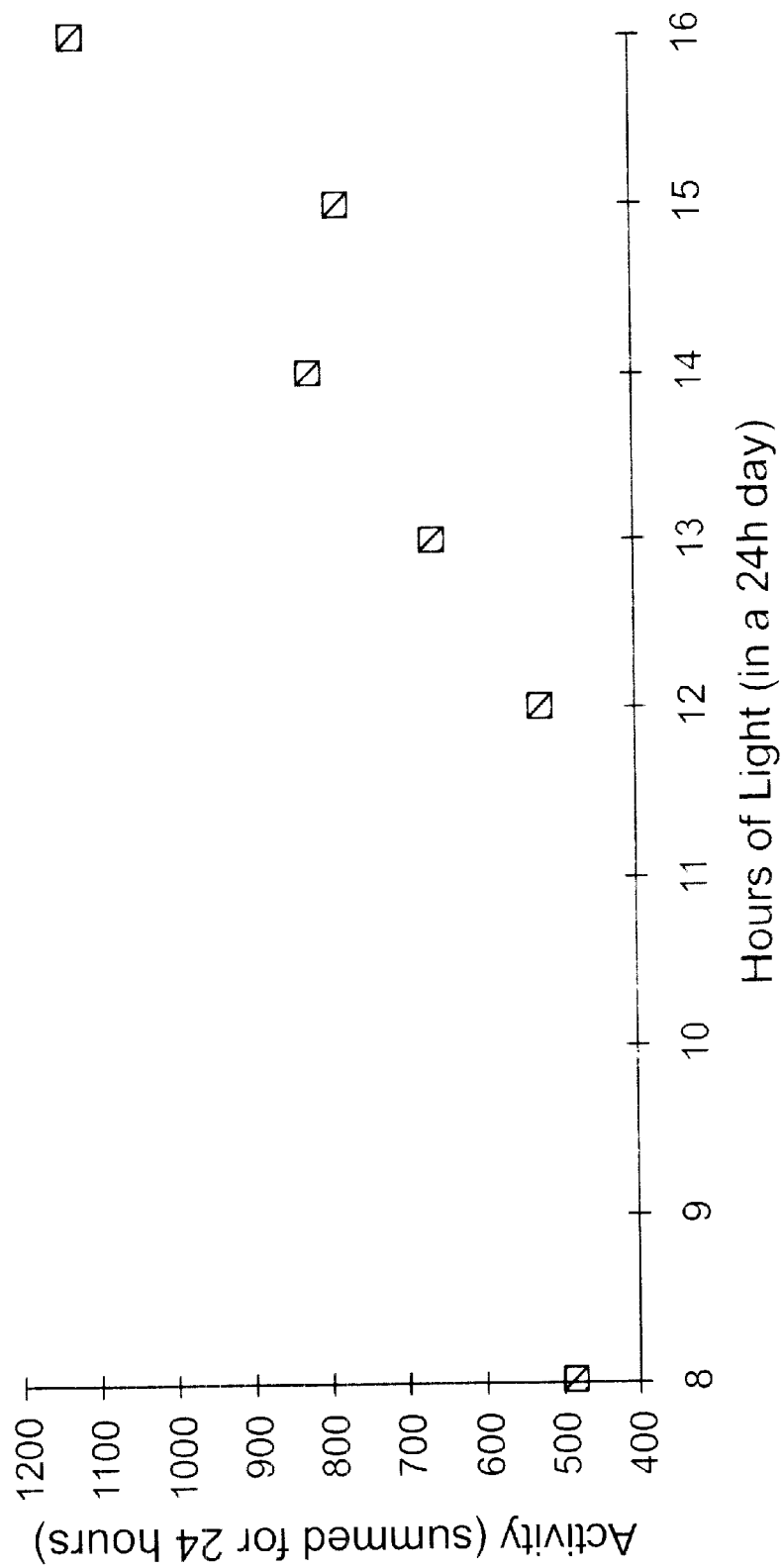
FIG. 9 shows the change in activity of worms over different photophases.

The representative results are summarised in FIG. 9. The activity of the animals was substantially greater than that recorded for animals in the LD 8:16 and LD 12:12 light dark cycles in all of those in which the duration of the photophase was greater than 12 hours; most of this activity occurred during the hours of darkness. The activity of the animals in the experimental chambers was recorded by means of a time lapse controlled far-red sensitive video camera which showed that the activity of the animals at night comprised principally food searching behaviour. The activity pattern as indicated by the mean number of actions per hour was progressively greater in those animals exposed to LD cycles in which the photophase was progressively greater than 12 hours and in which the duration of the photophase was progressively less than 16 hours.

EXAMPLE 4

Figure 10:
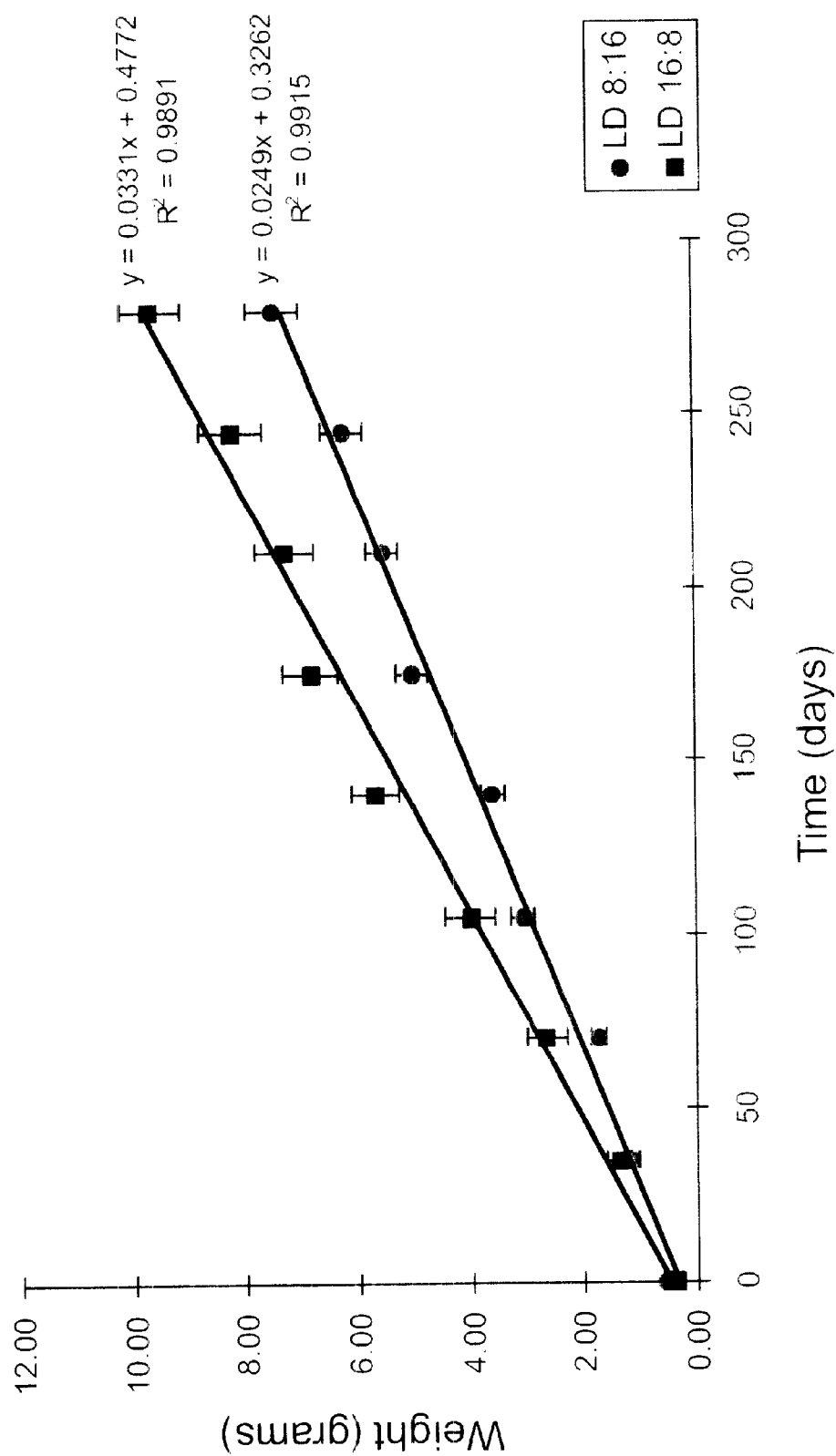
FIG. 10 shows the increase in weight over time for worms experiencing a long day or a short day photophase.

In a further embodiment of the invention the growth of juvenile *Nereis virens* was recorded for a period of 6 months under LD 8:16 and LD 16:8. The biomass of the animals exposed to the LD cycle 16:8 was substantially greater at each stage of the experiment than that of animals exposed to LD 8:16. The resulting data are shown in FIG. 10.

Modifications and improvements can be incorporated without departing from the scope of the invention. The data establishes that the behavioural activity, prospecting for food and growth and regeneration of marine worms is influenced by the duration of periods of light in a 24 hour day and that these measures of activity and growth may be materially altered by artificially changing the duration of periods of lightness and darkness. In the embodiment described for *Nereis virens* maximum growth occurs during the subjective summer and is reduced during the natural winter in animals that are kept at constant temperature and provided with food ad libideo. In other marine worms the timing of periods of maximum growth may be different and the duration of the periods of light and of dark in the 24 hour LD cycle needed to maximise growth rate and/or feeding rate may differ from that described for *Nereis virens*, but such modifications do not depart from the scope of the invention.

What is claimed is:

1. A method of controlling the growth of polychaete (Polychaeta) worms of the Nereidae family or Eunicidae family, said method comprising controlling the light to which the worms are exposed.

2. A method in accordance with claim 1 in which the worms are maintained in a controlled temperature regime.

3. A method in accordance with claim 1 in which the worms have an effective date of birth other than during the natural breeding season.

4. A method in accordance with claim 1 in which the worms are recovered from a preservation system.

5. A method in accordance with claim 1 in which the worms have been induced to breed outside the normal breeding period.

6. A method in accordance with claim 1, in which the duration of the photophase is controlled.

7. A method in accordance with claim 1, in which the duration of the scotophase is controlled.

8. A method in accordance with claim 7 in which the duration of the scotophase is less than that occurring in the natural photoperiodic regime.

9. A method in accordance with claim 1 in which the photoperiodic regime to which the worms are exposed is one in which the duration of the photophase is greater than that occurring in the natural photoperiodic regime.

10. A method according to claim 1, in which the duration of the photophase is constant.

11. A method according to claim 1, in which the duration of the scotophase is constant.

12. A method according to claim 1, using artificial light.

13. A method according to claim 1, using natural light.

14. A method according to claim 1, wherein the duration of the scotophase is controlled by interfering with the ingress of natural light.

15. A method in accordance with claim 1 in which the worms belong to the Nereidae family.

16. A method in accordance with claim 15 in which the worms are of the species *Nereis* (*Neanthes*) *virens*.

17. A method in accordance with claim 1 in which the worms belong to the family Eunicidae.

18. A method in accordance with claim 17 in which the worms are members of the genus Marphysa.

19. A method of controlling growth in polychaete worms of the Nereidae family or the Eunicidae family, said method comprising exposing them to artificially extended day lengths or to artificially shortened periods of darkness.

20. A method according to claim 19, wherein the worms' growth is controlled during periods of predominantly short day lengths.

21. A method of controlling growth in polychaete worms of the Nereidae family or the Eunicidae family, said method comprising exposing them to photoperiodic regimes that mimic the effects of exposing them to extended day lengths or to shortened periods of darkness.

22. A method of controlling growth in polychaete worms of the Nereidae family or the Eunicidae family, said method comprising exposing them to artificially shortened day lengths or to artificially extended periods of darkness.

23. A method of controlling growth in polychaete worms of the Nereidae family or the Eunicidae family, said method comprising exposing them to photoperiodic regimes that mimic the effects of exposing them to shortened day lengths or to extended periods of darkness.

\* \* \* \* \*